United States Patent [19]
Weinkauf et al.

[11] Patent Number: 6,022,896
[45] Date of Patent: *Feb. 8, 2000

[54] PETROSELINIC ACID AS AN ANTI-IRRITANT IN COMPOSITIONS CONTAINING ALPHA-HYDROXY ACIDS

[75] Inventors: Ronni Weinkauf, River Edge; Uma Santhanam, Tenafly; Laura Rose Palanker, Jackson; Thomas Eugene Januario, Ridgefield, all of N.J.; Anita Brinker, Wilmington, Del.

[73] Assignee: Chesebrough-Pond's USA Co., Greenwich, Conn.

[ * ] Notice: This patent issued on a continued prosecution application filed under 37 CFR 1.53(d), and is subject to the twenty year patent term provisions of 35 U.S.C. 154(a)(2).

[21] Appl. No.: 09/150,841

[22] Filed: Sep. 10, 1998

[51] Int. Cl.[7] ............................. A61K 31/19; A61K 31/20
[52] U.S. Cl. ............................................. 514/557; 514/560
[58] Field of Search ...................................... 514/557, 560

[56] References Cited

U.S. PATENT DOCUMENTS

| | | | |
|---|---|---|---|
| 4,966,754 | 10/1990 | Purohit et al. | 424/195.1 |
| 5,380,894 | 1/1995 | Burg et al. | 554/219 |
| 5,422,371 | 6/1995 | Liao et al. | 514/560 |
| 5,516,793 | 5/1996 | Duffy | 514/474 |
| 5,558,871 | 9/1996 | Griat et al. | 424/401 |
| 5,679,374 | 10/1997 | Fanchon et al. | 424/450 |
| 5,733,572 | 3/1998 | Unger et al. | 424/450 |
| 5,807,820 | 9/1998 | Elias | 514/11 |
| 5,866,040 | 2/1999 | Nakama et al. | 252/312 |

FOREIGN PATENT DOCUMENTS

| | | |
|---|---|---|
| 116 439 | 8/1984 | European Pat. Off. . |
| 248 701 | 12/1987 | European Pat. Off. . |
| 355 842 | 2/1990 | European Pat. Off. . |
| 0 631 772 | 1/1995 | European Pat. Off. . |
| 0 709 084 | 8/1995 | European Pat. Off. . |
| 888 773 | 1/1999 | European Pat. Off. . |
| 197 03 745 | 8/1998 | Germany . |
| 98/16104 | 4/1998 | WIPO . |
| 98/53698 | 12/1998 | WIPO . |

OTHER PUBLICATIONS

International Search Report in the application of PCT/EP 99/01565 (Jul. 1999).
Chemical Abstract, vol. 87, No. 24, Dec. 12, 1977, Columbus, Ohio, US, No. 87:189308S.
Derwent abstract of EP 248 701 Dec. 1987.
Derwent abstract of DE 197 03 745 Jun. 1998.
Derwent abstract of RU 2027440, Aug. 11, 1992.
Derwent abstract of CS 245821, Oct. 16, 1986.
Afifi et al., "Some Pharmacological Activities of Essential Oils of Certain Umbelliferous Fruits", Vet. Med. J., Giza., vol. 42, No. 3 pp. 85–92 (1994).
Yagaloff et al., "Essential Fatty Acids are Antagonists of the Leukotriene $B_4$ Receptor", Prostaglandins Leukotrienes and Essential Fatty Acids, 52, pp. 293–297 (1995).
Devchand et al., "The PPAR60 –Leukotriene $B_4$ pathway to inflammation control", Nature, vol. 384, pp. 39–43 (1996).
Keller et al., "Fatty acids and retinoids control lipid metabolism through activation of peroxisome proliferator–activated receptor–retinoid X receptor heterodimers", Proc. Natl. Acad. Sci. USA 90, pp. 2160–2164 (1993).

*Primary Examiner*—Raymond Henley, III
*Attorney, Agent, or Firm*—Rimma Mitelman

[57] ABSTRACT

Compositions containing alpha hydroxy acids and further containing petroselinic acid as an anti-irritant/anti-sting agent.

4 Claims, No Drawings

PETROSELINIC ACID AS AN ANTI-IRRITANT IN COMPOSITIONS CONTAINING ALPHA-HYDROXY ACIDS

FIELD OF THE INVENTION

The present invention relates to the use of petroselinic acid in a composition and in a method for reducing or eliminating skin irritation or sting induced by alpha hydroxy acids.

BACKGROUND OF THE INVENTION

Alpha hydroxy acids (AHAs) have been proven to deliver cosmetic benefits, such as improvement in the appearance of photodamaged or naturally aged skin, skin lightening, treatment of age spots, etc. Unfortunately, their use at high concentrations may occasionally be associated with skin irritation, e.g. skin redness and stinging sensation upon application. See e.g. Kligman A. M., J. Geriatr. Dermatol. 1997; 5(3): 128–131). The irritation can be ameliorated by lowering the amount of an active ingredient in the composition or by reducing the active's penetration through the skin. A serious drawback of both approaches is that the efficacy is impaired. The AHA irritation can be reduced by raising the composition's pH but this method yields reduced efficacy due to a decreased AHA penetration through the skin. It is desirable to reduce or eliminate the irritation potential of AHAs while maintaining their efficacy.

European Patent Application 0631722 (Johnson & Johnson) discloses the use of glycolic acid to reduce irritation of the skin by retinol. U.S. Pat. No. 5,516,793 (Duffy) discloses the use of ascorbic acid to ameliorate the irritation caused by various topical ingredients, including AHAs.

Use of oils rich in petroselinic acid e.g coriander seed oil in cosmetic compositions for skin has been disclosed (EP 0709084 A2). EP 0709084 teaches the use of coriander seed oil as a moisturizing agent but does not disclose the property of petroselinic acid to reduce irritation. In addition, the optional presence of various additives is mentioned, e.g. keratolytic agents such as hydroxyacids (n-octanoyl 5-salicylic acid). Salicylic acid is a beta-hydroxy acid, which is known to act in a manner different from alpha hydroxy acids and is believed to be less irritating.

The art discussed above does not disclose combinations of AHAs and coriander seed oil or petroselinic acid in cosmetic compositions and does not appear to teach the use of petroselinic acid to reduce irritation or sting associated with the use of AHAs.

SUMMARY OF THE INVENTION

The present invention includes, in part, a composition containing an alpha hydroxy acid ("AHA") and further containing petroselinic acid.

The invention also includes a method for reducing irritation or sting induced by the topical application of a composition containing AHAs, the method comprising topically applying petroselinic acid to reduce irritation induced by the composition. According to the inventive method, petroselinic acid may be co-present with AHAs in the same composition, or petroselinic acid may be applied from a separate composition.

According to the present invention, by virtue of topical application of petroselinic acid, the irritation or sting induced by the topical application of AHAs is reduced or eliminated. It has been found as part of the present invention that not all known anti-irritants, ameliorate AHA induced irritation.

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about." All amounts are by weight of the composition unless otherwise specified.

Petroselinic acid ($CH_3(CH_2)_{10}CH=CH(CH_2)_4COOH$) is an essential ingredient of the inventive compositions.

The amount of petroselinic acid in the inventive compositions ranges generally from 0.05% to 20% by weight of the composition, preferably from 0.1% to 10%, most preferably from 0.5% to 5%.

AHAs enhance proliferation and increase ceramide biosynthesis in keratinocytes, increase epidermal thickness, and increase desquamation of normal skin resulting in smoother, younger looking skin.

The AHA can be a combination of stereoisomers (DL, D or L).

AHAs have the general structure (1):

where M is hydrogen or a saturated or an unsaturated, straight or branched hydrocarbon chain containing from 1 to 27 carbon atoms.

Even more preferably the hydroxy acid is chosen from lactic acid, 2-hydroxyoctanoic acid, hydroxylauric acid, glycolic acid, and mixtures thereof. When stereo isomers exist, L-isomer is most preferred.

It is to be understood that depending on the pH of the composition, the hydroxy acid may be present as a salt, e.g. ammonium or potassium or sodium salt.

Although the inventive compositions may have any pH in the general range of 2.5 to 10, the inventive compositions are particularly useful when they are at an acidic pH (especially if they contain a hydroxy acid), most preferably at a pH of 3–4, because such compositions are particularly efficacious. Unfortunately, at this pH the compositions are also irritating.

A particular advantage of the inventive compositions is that higher amounts of hydroxy acids or retinoids may be employed without causing skin irritation. Preferably the amount of the hydroxy acid component present in the composition according to the invention is from 0.01 to 20%, more preferably from 0.1 to 12% and most preferably from 2 to 12% by weight.

Most preferred inventive compositions containing petroselinic acid anti-irritant include glycolic acid and/or lactic acid because these ingredients have been found to cause irritation yet they were found to be particularly efficacious at delivering cosmetic benefits.

The skin treatment composition of the invention also includes a cosmetically acceptable vehicle or a carrier which is inert, usually an ingredient present in the highest amounts, and functioning to deliver active or performance ingredients.

Vehicles other than water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5 to 95%, preferably from 25 to 90% by weight of the composition. The amount of vehicle may range from about 2 to about 99 wt %, preferably from about 50 to about 99%, most preferably from about 80 to 99%, by weight of the total composition.

According to the present invention, the vehicle is preferably at least 60 wt. % water, by weight of the vehicle. The inventive compositions are preferably oil-water emulsions, in order to improve dermal delivery of hydroxy acids (See Sah A., "An in-vitro study of the effect of formulation variables and product structure on the delivery of alpha-hydroxy acid (Lactic acid) to skin", MS Thesis, Department of Pharmaceutical Sciences of the College of Pharmacy, University of Cincinnati, Ohio, July 1996). Such improved delivery is frequently accompanied by increased irritation/ sting, making the use of petroselinic acid in such emulsions particularly critical. In the preferred oil-in-water emulsions according to the present invention, water comprises at least 50 wt. % of the inventive emulsion, most preferably from 50 to 70 wt. %, by weight of the composition.

Optional Skin Benefit Materials and Cosmetic Adjuncts

Various types of active ingredients may be present in cosmetic compositions of the present invention. Actives are defined as skin benefit agents other than emollients and other than ingredients that merely improve the physical characteristics of the composition. Although not limited to this category, general examples include anti-wrinkle compounds and sunscreens and tanning agents.

Sunscreens include those materials commonly employed to block ultraviolet light. Illustrative compounds are titanium dioxide, the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B.F. Goodrich Company. Gums may be employed such as xanthan, carrageenan, gelatin, karaya, pectin and locust bean gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, Fullers earth, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other component materials may range anywhere from 0.001% up to 20% by weight of the composition.

Use of the Composition

The composition according to the invention is intended primarily as a product for topical application to human skin, especially as an agent for conditioning and smoothening the skin, and preventing or reducing the appearance of wrinkled or aged skin.

In use, a small quantity of the composition, for example from 1 to 10 ml, is applied to exposed areas of the skin, from a suitable container or applicator and, if necessary, it is then spread over and/or rubbed into the skin using the hand or fingers or a suitable device.

According to the present inventive method, the skin irritation induced by the active ingredient is reduced or eliminated by topical application of petroselinic acid. Petroselinic acid may be co-present with the active, or it may be applied to the skin separately from the active.

Product Form and Packaging

The topical skin treatment composition of the invention can be formulated as a lotion, a fluid cream, a cream or a gel. The composition can be packaged in a suitable container to suit its viscosity and intended use by the consumer. For example, a lotion or fluid cream can be packaged in a bottle or a roll-ball applicator, or a capsule, or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a cosmetically acceptable composition as herein defined.

Petroselinic acid may be packaged separately from the composition containing AHAs.

The following specific examples further illustrate the invention, but the invention is not limited thereto.

COMPARATIVE EXAMPLE 1

An emulsion base was prepared having the following formula.

EMULSION BASE FORMULA

| FULL CHEMICAL NAME OR CFTA NAME | TRADE NAME AND % ACTIVE AS RECEIVED | WT. % |
| --- | --- | --- |
| water, DI | | 46.54 |
| disodium EDTA | Sequesterene Na2 | 0.05 |
| magnesium aluminum silicate | Veegum Ultra | 0.6 |
| methyl paraben | Methyl Paraben | 0.15 |
| dimethicone | DC Antiform Emulsion | 0.01 |
| butylene glycol 1,3 | Butylene Glycol 1,3 | 3.0 |
| hydroxyethylcellulose | Natrosol 250HHR | 0.5 |
| glycerine, USP | Glycerine USP | 2.0 |
| xanthan gum | Keltrol 1000 | 0.2 |
| triethanolamine | Triethanolamine 99 (%) | 1.2 |
| stearic acid | Pristerene 4911 | 3.0 |
| propyl paraben NF | Proplyparaben NF | 0.1 |
| glyceryl hydrostearate | Naturechem GMHS | 1.5 |
| stearyl alcohol | Lanette 18DEO | 1.5 |
| isostearyl palmitate | Protachem ISP | 6.0 |
| C12–15 alcohols octanoate | Hetester FAO | 3.0 |
| dimethicone | Silicone Fluid 200 (50 cts) | 1.0 |
| cholesterol NF | Cholesterol NF | 0.5 |
| sorbitan stearate | Sorbitan Stearate | 1.0 |
| butylated hydroxytoluene | Embanox BHT | 0.05 |
| tocopheryl acetate | Vitamin E Acetate | 0.1 |
| PEG-100 stearate | MYRJ 59 | 2.0 |

-continued

| EMULSION BASE FORMULA | | |
|---|---|---|
| FULL CHEMICAL NAME OR CFTA NAME | TRADE NAME AND % ACTIVE AS RECEIVED | WT. % |
| solium stearoyl lactylate | Pationic SSL | 0.5 |
| retinyl palmitate | Vit A Palmitrate 84% | 0.06 |
| hydroxy caprylic acid | Hydorxy caprylic acid | 0.1 |
| water, DI | | q.s. to 99.80 |
| alpha-bisabolol | Alpha-bisabolol | 0.2 |
| pH | | 7–8 |

Additional ingredients in Table 1 below were added in place of water.

Subjects were tested according to Irritation Test Method described below.

Irritation Test Method

Four Exposure Patch Test: The objective was to compare the level of irritation produced by various test materials after repeated patch applications. The test materials were held in contact with the skin under occlusive conditions. The outer upper arm of the panelist was designated as the area of application. Bandage type dressing (Scanpor® tape) was used to hold the patches (25 mm Hill Top® Chamber fitted with 18 mm diameter disc of Webril® padding) into place. Both upper arms of the panelist were used. Patches were applied in a balanced random order.

Patches were applied at 9:00 o'clock Monday morning and removed at 9:00 o'clock Tuesday morning (24 hour exposure). A new set of patches was applied at 3:00 o'clock Tuesday afternoon and removed Wednesday morning at 9:00 o'clock (18 hour exposure). A third set of patches was applied at 3:00 o'clock Wednesday afternoon and removed Thursday morning at 9:00 o'clock (18 hour exposure). A final set of patches was applied at 3:00 o'clock Thursday afternoon and removed Friday morning at 9:00 o'clock (18 hour exposure).

Each time the patches were removed, the sites were rinsed with warm water and patted dry. The test sites were then marked with a surgical skin marking pen to ensure location for grading and subsequent patch applications. Test sites were evaluated at 3:00 p.m. on Tuesday, Wednesday, Thursday and Friday of the study, prior to re-patching.

Skin irritation such as moderate redness, dryness, and/or itching of the test site is expected. Swelling of the test sites is possible. If any test has moderate redness or any swelling at evaluation, that particular test site should not be repatched.

The test sites on each arm were visually ranked by two trained examiners under consistent lighting. The test sites were ranked in order of severity. The examiner ranking responses at the first evaluation period continued ranking the sites each day throughout the study.

In ranking the reactions, the site with the most severe response was given the lowest score. The site with the second most severe response was given the second lowest score, etc. There was no forced ranking. If two or more sites had no response or the same response (no difference between sites), an average of the ranks was assigned. If a site has been discontinued due to degree of irritation the site retained the rank it received at the time dosing was discontinued.

Statistical Analysis

The ranking results from the patch treatments were statistically compared by nonparametric statistical methods. The test materials containing the anti-irritants were compared to the corresponding control containing only hydroxy acid and/or retinoid, using Friedman's Rank Sum. Treatments were compared to the Formula 2 (control) at each evaluation point using Friedman's analysis with the panelist acting as a block (i.e., each panelist was tested with each test treatment). p-value of<0.1 was considered statistically significant.

Compositions containing ingredients as indicated in Table 1 were tested using the Irritation Test Method. 20 subjects were tested. The higher the Sum of Ranks, the less severe the irritation.

TABLE 1

Irritation Test Results

| COMPOSITION | INGREDIENTS | SUM OF RANKS (DAY 4) |
|---|---|---|
| 1 | Base Formula | 68.5* |
| 2 | Control: Base Formula + 8% Glycolic Acid and 0.075% Retinol | 46.5 |
| 3 | Composition #2 + 3% Black Currant Seed Oil | 58.0 |
| 4 | Composition #2 + 1% Sambucus | 44.5 |

*Significantly less irritating than composition #2.

It can be seen from the results in Table 1 that after four exposures, 8% glycolic acid with 0.075% retinol (#2) was significantly more irritating than Base formula #1. 1% Sambucus or 3% Black Currant Seed Oil did not significantly reduce the irritation. Even though irritation caused by alpha-hydroxy acid is a problem that cannot be solved by applying even such well-known anti-irritants as Sambucus and Black Currant.

COMPARATIVE EXAMPLE 2

Compositions 1, 5 and 11–14 containing ingredients as indicated in Table 2 were tested using the Irritation Test Method described in Example 1. Seventeen subjects were tested. The results that were obtained are summarized in Table 2. The higher the sum of ranks, the less is the irritation.

TABLE 2

Irritation Test Results

| COMPOSITION # | INGREDIENTS | SUM OF RANKS (DAY 4) |
|---|---|---|
| 1 | Base Formula | 74.5$^a$ |
| 5 | Base Formula + 8% Glycolic + 0.075% Retinol | 61.5 |
| 11 | Composition #5 + 1% Green Tea | 51.0 |
| 12 | Composition #5 + 0.1% K2 Glycyrrhetinic Acid | 54.5 |
| 13 | Composition #5 + 3% Quench T* | 58.5 |
| 14 | Composition #5 + 3% Polyol Prepolymer-2** | 57.0 |

$^a$Statistically less irritating than composition #5.
*An anti-irritant from Centerchem (containing water, butylene glycol, kola bean extract, guarana extract, and mate extract).
**An anti-irritant from Penederm, Inc. (CFTA name PPG-12/SMDI).

It be seen from the results in Table 2 that none of the known anti-irritants tested were able to significantly reduce the irritation induced by composition #5 (containing 8% Glycolic Acid and 0.075% Retinol).

EXAMPLE 3

This example demonstrates that topical application of AHAs releases IL1-alpha from stratum corneum.

It is known that the stratum corneum is a storehouse of the proinflammatory cytokine IL-1α (L. Wood, P. Elias, C. Calhoun, J. Tsai, C. Grunfeld, K. Feingold. Barrier Disruption Stimulates Interleukin −1α Expression and Release from a Pre-Formed Pool in Murine Epidermis J. Invest. Dermatol. 106:397–403, 1996). The following example illustrates that topical application of AHAs induces the release of IL-1α in human skin.

Ex Vivo Immunohistochemical Staining of IL-1α:

Human cadaver skin was treated with Base Formula (see comparative example 1) further containing 8% Glycolic acid (GA), pH 3.8, or vehicle cream (Base Formula) or an aqueous solution of 8% Lactic acid (LA), pH 3.8, or Tris buffer (pH 7.6) for 30 minutes on ice. 8 mm punch biopsies were taken and fixed in formalin. 5μ sections were incubated with polyclonal anti-human IL-1α (R&D Systems, 1/50 dilution) and developed using the avidin-biotin-horse-radish peroxidase complex procedure according to the manufacturer's instructions (Vector Labs) and 3-amino-9-ethyl carbazole as the chromogen. The intensity of positive labeling (% area stained) for IL-1α was quantitated using ImagePro Plus version 3 (Media Cybernetics, Silver Spring, Md.). The results that were obtained are summarized in Table 3.

TABLE 3

|  | 8% Lactic | Tris Buffer | 8% Glycolic cream | Vehicle cream |
|---|---|---|---|---|
| % Area Stained | 42.7 ± 12* | 14.2 ± 10.4 | 48.4 ± 15.4** | 2.5 ± 1.7 |

*Significant compared to Tris buffer by t -test, p < 0.01
**Significant compared to vehicle by t -test, p < 0.03

It can be seen from the results in Table 3 that treatment with 8% lactic acid increased IL-1α staining compared to its control Tris buffer. In addition, 8% glycolic acid cream elicited a significant increase in IL-1α staining relative to vehicle. Topical application of the AHAs, (glycolic acid and L-lactic acid) appeared to stimulate an immediate release of IL-1α in the epidermis. The stratum corneum appears to be the most obvious source as high levels of IL-1α are known to be stored in/around corneocytes.

The IL-1α released following AHA treatment is capable of triggering the arachidonic acid cascade, which converts arachidonic acid into a variety of inflammatory metabolites such as Prostaglandin E2 (PGE2). The prostaglandins play a central role in inflammation and are therefore pertinent to the pathogenesis and treatment of irritation (Kupper T, in Immunology: The Role of Cells and Cytokines in Immunity and Inflammation" Oppenheim J. J. and Shevach E. J., eds. Oxford University press, New York, 1990, pp 285–305).

EXAMPLE 4

The following example demonstrates that petroselinic acid can effectively inhibit the induction of PGE2 caused by IL-1α, which in turn is released by AHAs. Therefore, petroselinic acid would be effective in reducing the irritation caused by AHAs.

Neonatal human dermal fibroblasts (passage 5–9) were seeded at a density of 7500 cells per well in 96-well tissue culture treated plates (Corning-Costar, Corning, N.Y.). The medium used was Dulbecco's Modified Eagle's Medium (DMEM), high-glucose (Gibco/Life Technologies, Gaithersburg, Md.) supplemented with 2 mM L-glutamine, 10% fetal bovine serum, and antibiotic and anti mycotic solutions (all also Life Technologies). After 48 hours. each well was rinsed twice with 200 μl serum-free DMEM and the cells dosed with 200 μl in DMEM+L-glutamine containing IL-1 alpha at 1 ng/ml and/or active. After six hours, cells were examined microscopically for qualitative viability, and the medium was harvested and frozen until analysis. Each treatment was run in quadruplicate.

Enzyme immunoassay was performed using a commercial PGE2 kit (Amersham, Buckinghamshire, England). PGE2-specific antibody is precoated on a set of microtiter wells. The assay is based on the competition between unlabelled PGE2 (standard or sample) and a fixed quantity of peroxidase labeled PGE2 for a limited amount of the well-bound PGE2-specific antibody. Standards of 0, 1, 2, 4, 8, 16, and 32 pg/well or 50 μl media/well were applied with 50 μl/well of 0.1 M phosphate buffer pH 7.5 for 3 hours at 40° C. At the end of this incubation, 50 μl/well of horse-radish peroxidase-conjugated PGE2 was added to all wells and the plate incubated for 1 hour at 4° C. Plates were washed 4 times with 300 μl/well 0.01 M phosphate buffer pH 7.5 containing 0.5% Tween 20. 150 μl/well 3,3',5,5'-tetramethylbenzidine/hydrogen peroxide substrate in 20% dimethylformamide was added and the plate incubated exactly 30 minutes at room temperature. Reaction was stopped by adding 100 μl/well 1 M sulfuric acid. The Dynatech MR7000 microplate spectrophotometer (Dynatech, Chantilly, Va.) was used to quantitate color in the wells by reading absorbance at 450 nm. A standard curve was plotted and the amount of PGE2 in the samples was extrapolated from the curve.

The anti-inflammatory potential of the test compounds was assessed by the ability of the compound to inhibit IL-1 alpha-induced PGE2. Statistical significance was determined using the student's t-test. The results that were obtained are summarized in Table 4.

TABLE 4

| treatment | PGE 2 pg/ml | % decreased compared to IL-1α |
|---|---|---|
| control | 267.6 ± 48.6 | |
| IL-1α | 598.2 ± 118.3 | |
| IL-1α + petroselinic at 0.01% | 201.2 ± 40.1 | 120%* |
| IL-lα + petroselinic at 0.001% | 308.3 ± 97.2 | 80% |

*Statistically significant at p < 0.05 compared to value for IL-lα alone.

It can be seen from the results in Table 4 that petroselinic acid can effectively inhibit the induction of PGE2 caused by IL-1 alpha, which in turn is released by AHAs. Therefore, petroselinic acid would be effective in reducing the irritation caused by AHAs.

Examples 5–8 illustrate topical compositions according to the present invention. The compositions can be processed in conventional manner. They are suitable for cosmetic use. In particular the compositions are suitable for application to wrinkled, rough, dry, flaky, aged and/or UV-damaged skin to improve the appearance and the feel thereof as well as for application to healthy skin to prevent or retard deterioration thereof.

EXAMPLE 5

A typical oil-in-water emulsion within the scope of the invention is as follows:

| CHEMICAL NAME | WT. % |
|---|---|
| propylene glycol | 1 |
| glycerin | 1 |
| hydroxyethylcellulose | 0.5 |
| magnesium aluminum silicate | 0.5 |
| imidazolidinyl urea | 0.5 |
| tetrasodium EDTA | 0.05 |
| petrolatum | 2 |
| isopropyl palmitate | 5 |
| dimethicone | 0.5 |
| cholesterol | 0.5 |
| cetyl alcohol | 0.5 |
| isostearic acid | 3 |
| retinyl palmitate | 0.1 |
| peg-40 stearate | 1 |
| peg-100 stearate | 1 |
| sorbitan stearate | 1 |
| petroselinic acid | 0.5 |
| glycolic acid | 7 |
| ammonium hydroxide | to pH 4.0 |
| water DI | qs to 100% |

EXAMPLE 6

Another typical oil-in-water emulsion within the scope of the invention is as follows:

| CHEMICAL NAME | WT. % |
|---|---|
| propylene glycol | 1 |
| hydroxyethylcellulose | 0.5 |
| magnesium aluminum silicate | 0.5 |
| imidazolidinyl urea | 0.2 |
| petrolatum | 2 |
| isopropyl palmitate | 5 |
| dimethicone | 0.5 |
| cholesterol | 0.5 |
| stearic acid | 3 |
| isostearic acid | 1.5 |
| glycerol stearate | 1.5 |
| peg-40 stearate | 1 |
| peg-100 stearate | 1 |
| sorbitan stearate | 1 |
| cetyl alcohol | 0.5 |
| petroselinic acid | 2 |
| glycolic acid | 10 |
| ammonium hydroxide | to pH 3.8 |
| water DI | qs to 100% |

EXAMPLE 7

A typical water-in-oil dispersion within the scope of the invention is as follows:

| CHEMICAL NAME | WT. % |
|---|---|
| isostearyl neopentanoate | 20 |
| peg-8 caprylic/capric glycerides | 6 |
| cetyl octanoate | 17 |
| polyglyceryl-6 dioleate | 15 |
| cyclomethicone | 20 |
| glyceryl isostearate | 0.5 |
| isostearic acid | 0.5 |
| ceramide III | 0.1 |
| ppg-5-cetheth-20 | 3 |
| L-lactic acid/potassium lactate | 6 |

-continued

| CHEMICAL NAME | WT. % |
|---|---|
| hydroxycaprylic acid | 0.1 |
| water DI | 1.3 |
| petroselinic acid | 0.5 |

EXAMPLE 8

The following oil-in-water emulsion within the scope of the invention is prepared:

| CHEMICAL NAME | WT. % |
|---|---|
| xanthan gum | 0.2 |
| disodium EDTA | 0.1 |
| sodium PCA | 0.5 |
| diazodinyl urea | 0.3 |
| titanium dioxide | 1 |
| stearic acid | 3 |
| cyclomethicone | 0.3 |
| cetyl alcohol | 0.5 |
| glyceryl stearate | 0.5 |
| peg-100 stearate | 0.5 |
| steareth-2 | 0.2 |
| lecithin | 0.5 |
| tocopherol | 0.2 |
| octyl methoxycinnamate | 6 |
| petroselinic acid | 0.5 |
| glycolic acid | 3 |
| malic acid | 2 |
| lactic acid | 2 |
| green tea extract | 1 |
| triethanolamine | to pH 3.8 |
| water DI | qs to 100% |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A composition comprising:
   (i) an alpha hydroxy acid in an amount of from about 0.01 to about 20% by weight of the composition;
   (ii) petroselinic acid in an amount of from about 0.05% to about 20%, by weight of the composition; and
   (iii) a cosmetically acceptable vehicle.

2. The composition of claim 1 wherein the amount of the hydroxy acid is from about 0.1 to about 12% by weight of the composition.

3. The composition of claim 1 wherein the hydroxy acid benefit ingredient is selected from the group consisting of glycolic acid, lactic acid, and mixtures thereof.

4. A method for reducing sting or irritation induced by the topical application of a composition containing an alpha hydroxy acid, the method comprising topically applying petroselinic acid in an amount effective to reduce irritation induced by the composition.

* * * * *